United States Patent [19]

Hansen

[11] Patent Number: 4,463,862

[45] Date of Patent: Aug. 7, 1984

[54] THERMOPLASTIC CONTAINER

[76] Inventor: Gerhard Hansen, Heerstrasse 20, 7166 Sulzbach-Laufen, Fed. Rep. of Germany

[21] Appl. No.: 420,915

[22] Filed: Sep. 21, 1982

[30] Foreign Application Priority Data

Oct. 1, 1981 [DE] Fed. Rep. of Germany ....... 3139084

[51] Int. Cl.³ ................................................ A61M 5/14

[52] U.S. Cl. ........................................ 215/33; 215/232; 215/249; 604/415

[58] Field of Search .................... 215/32, 247, 249, 33, 215/232; 150/55; 604/415, 408

[56] References Cited

U.S. PATENT DOCUMENTS

| | | | |
|---|---|---|---|
| 2,372,181 | 3/1945 | Barr | 215/33 |
| 3,356,244 | 12/1967 | Witchell | 215/32 |
| 4,011,961 | 3/1977 | Widen et al. | 215/249 X |
| 4,307,761 | 12/1981 | Tanokura | 215/247 X |

FOREIGN PATENT DOCUMENTS

| | | | |
|---|---|---|---|
| 2027749 | 12/1971 | Fed. Rep. of Germany | 215/247 |
| 835395 | 5/1960 | United Kingdom . | |
| 1526061 | 9/1978 | United Kingdom . | |

*Primary Examiner*—Donald F. Norton

*Attorney, Agent, or Firm*—Roylance, Abrams, Berdo & Goodman

[57] ABSTRACT

A thermoplastic container, particularly a bottle, has a one-piece container top unitarily formed with the container body and a container neck and enclosing a stopper of elastomeric material, particularly rubber. To prevent contact between the container contents and the stopper, a mounting and separating element is provided between the stopper and the container. The mounting element has tubular axially extending plug and retaining portions and has one edge which can be welded to the container and a radially projecting, thin weld ring.

12 Claims, 3 Drawing Figures

THERMOPLASTIC CONTAINER

This invention relates to a thermoplastic container and, particularly, a container such as a bottle having particular utility for containing intravenous solutions for parenteral administration directly from the container.

BACKGROUND OF THE INVENTION

In containers which are designed to hold solutions for parenteral applications, it is often necessary to provide a stopper of a kind which can be pierced and which has self-sealing characteristics. When such a stopper is used, it is usually necessary to provide a diaphragm to isolate the stopper from the contents of the container because the stopper characteristics are not consistent with reliable sealing over a long period of time. A diaphragm for this purpose is frequently configured as a curved or planar plastic disk such as those shown in Swiss Pat. No. 373,868 and U.S. Pat. No. 2,580,836.

It is also known to use a container having a closed top and to apply a penetrable screw cap to it with a seal therebetween such as shown in German Gebrauchsmuster No. 69 30 705. In this case, the container top separates the contents of the container from the seal.

BRIEF DESCRIPTION OF THE INVENTION

An object of the present invention is to provide a diaphragm which prevents contact of the resealable stopper with the contents of the container, and to so configure the diaphragm that it can be inserted during manufacture of the container, as by a blow-molding process, by simple insertion of the stopper assembly into the neck of the container.

Briefly described, the invention includes, an improved thermoplastic container such as a bottle of the type having a body portion, a unitary top portion, a unitary neck portion between the body and top portions and stopper means in the top portion. The stopper means includes an elastomeric stopper member and a stopper support body. The stopper support body has a diaphragm portion extending across the neck portion and a generally tubular retaining portion extending axially from the diaphragm portion in a direction opposite from the body portion and forming a chamber receiving the stopper member. The diaphragm extends between and separates the container contents and the stopper member. The retaining portion has a distal edge tapering to a thin edge to facilitate welding to the container top portion.

By forming the container in this manner, its manufacture is facilitated. The diaphragm is configured simply and, during the manufacture of the container, can easily be placed mechanically or by hand during the blowing process. The diaphragm as well as the stopper can be pierced.

Other features of the invention relate to configurations of the separation element to produce a welded joint with the container, and to the separation below the stopper.

In order that the manner in which the foregoing and other objects are attained in accordance with the invention can be understood in detail, a particularly advantageous embodiment thereof will be described with reference to the accompanying drawings, which form a part of this specification, and wherein.

Figure 1:
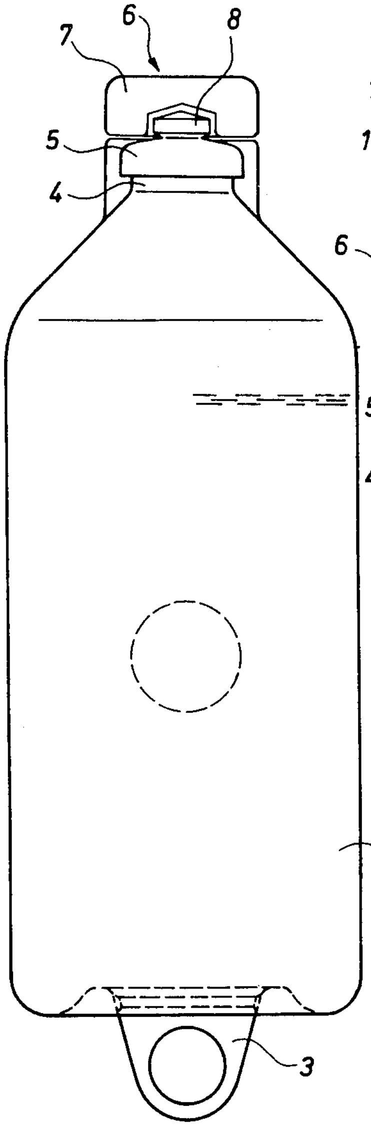
FIG. 1 is a side elevation of a container in accordance with the invention.

As shown in the drawings, the invention is applicable to a container such as a blow-molded, thermoplastic infusion bottle indicated generally at 1 which is filled and closed during the blowing process. The container includes a bottle body 2 which receives an infusion liquid, a suspension loop 3 at the bottom of body 2, a bottle neck 4, and a top portion 5 above the body 2 with a breakable cap 6 having a winged grip 7 mounted thereon, the grip 7 surrounding a top part 8 having a predetermined or defined breaking point.

As will be recognized, the terms "top" and "bottom" are used simply as a matter of convenience herein, and refer to the container in the orientation shown in the drawings. In use, the suspension loop would be at the top and the entire structure would be inverted from the positions shown in the figures.

Figure 2:
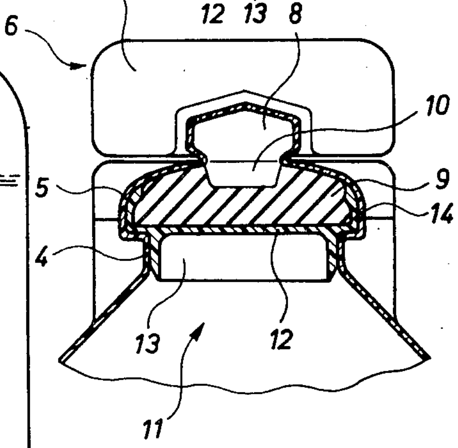
FIG. 2 is an enlarged partial side elevation, in partial section, of the top portion of the container of FIG. 1.

As illustrated in FIG. 2, the top portion 5 of the bottle contains a stopper 9 which is made of an elastomeric material, particularly rubber, which has the characteristics of being resealable, i.e., it is capable of reclosing after being pierced. Stopper 9 is formed with an indentation 10 in the center of its top surface as an attachment point for a discharge fitting.

Figure 3:
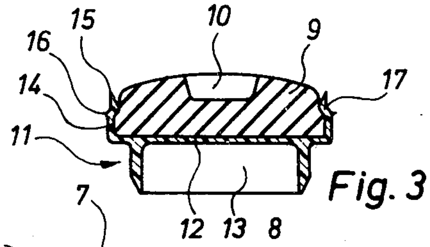
FIG. 3 is a side elevation of the stopper assembly portion of the structure of FIGS. 1 and 2 before incorporation into the container top.

Stopper 9 is mounted in a mounting part or element 11 which is also made of a thermoplastic material. Mounting element 11 has a central transversely extending portion in the nature of a membrane 12 which extends across the neck of the bottle. A tubular plug portion 13 extends axially away from the bottom surface of membrane 12 and has a diameter which is selected to fit into the bottle neck, the distal edge of tubular portion 13 being inwardly bevelled to facilitate insertion thereof into neck 4. On the side of membrane 12 opposite plug portion 13 is found an axially extending tubular portion 14 of larger diameter than plug portion 13, portion 14 being configured essentially tubular before it is inserted into the bottle, as illustrated in FIG. 3. As shown in FIG. 2, when the assembly has been placed into the bottle, it is fitted to the shape of top 5. The retaining portion 14 serves to receive and hold stopper 9 and has a shoulder which rests on the axially facing shoulder formed by neck 4 and top portion 5.

As shown in FIG. 3, the mounting part 14 has an edge 15 which is tapered to a relatively sharp annular edge and, on the outside surface, has a slightly projecting, relatively thin weld ring 16 approximately in the axial center of mounting portion 14. It can also be provided with a plurality of weld rings 16, axially spaced. Edge 15 and weld ring or rings 16 are so configured that they are welded to the plastic of the infusion bottle during manufacture. For this purpose, mounting element 11 is formed from a weldable plastic, preferably the same plastic as is used for the manufacture of bottle 1. In order to facilitate rapid welding, the free end of edge 15 which extends upwardly from stopper 9 and ring 16 when it is not inserted is tapered to an edge which has a thickness of, for example, about 0.1 mm. By the welding of mounting element 11 with the top 5, the liquid contained in bottle 1 is prevented from reaching stopper 9 and also from reaching into indentation 10.

An inwardly projecting bead 17 is provided on the inside of mounting part 14 to provide a locking connection of stopper 9 with mounting element 11 so that when a dispensing device with a suction element, not shown, is attached to stopper 9 and mounting element 11, it can be inserted into bottle 1 to somewhat beyond neck 4. Mounting part 14 is bent somewhat inwardly at an angle in the area of bead 17. Weld ring 16 is on the radially outwardly projecting portion of mounting part 14, opposite the bevelled part. As shown in FIG. 2, the edge of mounting part 14 which is free when the part has not yet been insert rests on stopper 9 and, on its outside, has the same shape as top 5.

Grip 7 and top part 8 are removed from the infusion bottle breaking the breakable cap 6. Recess 10 in stopper 9 is thus freely accessible from the outside. Stopper 9 and its membrane 12 can be pierced by a fitting for dispensing the contents. After removal of the dispensing fitting, the opening in stopper 9 which has been pierced closes automatically so that the infusion bottle is once again tightly closed and its contents separated from the atmosphere.

While one advantageous embodiment has been chosen to illustrate the invention, it will be understood by those skilled in the art that various changes and modifications can be made therein without departing from the scope of the invention as defined in the appended claims.

What is claimed is:

1. A thermoplastic container, such as a bottle, comprising a body portion;

a unitary top portion joined to said body portion by a unitary neck portion; and stopper means in said top portion including an elastomeric stopper member and a stopper support body, said stopper support body having a diaphragm portion extending across said neck portion; and a generally tubular retaining portion extending axially from said diaphragm portion in a direction opposite from said body portion and forming a chamber receiving said stopper member with said diaphragm portion between said stopper member and container contents in said body portion, said retaining portion having a distal edge tapering to a thin edge to facilitate welding to said top portion of the container.

2. A container according to claim 1 wherein said stopper support body comprises a tubular plug portion extending from said diaphragm portion in a direction opposite said receiving portion and into said neck portion, and comprises an axially facing shoulder at the junction of said neck and top portions.

3. A container according to claim 2 wherein the outer surface of said tubular retaining portion includes means defining at least one radially projecting, thin weld ring for welding to said top portion.

4. A container according to claim 3 wherein the inner surface of said tubular retaining portion includes means defining at least one radially projecting bead for engaging said stopper member.

5. A container according to claim 4 wherein a portion of said tubular retaining portion is bevelled inwardly in the area of said bead.

6. A container according to claim 2 wherein the inner surface of said tubular retaining portion includes means defining at least one radially projecting bead for engaging said stopper member.

7. A container according to claim 6 wherein a portion of said tubular retaining portion is bevelled inwardly in the area of said bead.

8. A container according to claim 1 wherein the outer surface of said tubular retaining portion includes means defining at least one radially projecting, thin weld ring for welding to said top portion.

9. A container according to claim 8 wherein the inner surface of said tubular retaining portion includes means defining at least one radially projecting bead for engaging said stopper member.

10. A container according to claim 9 wherein a portion of said tubular retaining portion is bevelled inwardly in the area of said bead.

11. A container according to claim 1 wherein the inner surface of said tubular retaining portion includes means defining at least one radially projecting bead for engaging said stopper member.

12. A container according to claim 11 wherein a portion of said tubular retaining portion is bevelled inwardly in the area of said bead.

* * * * *